(12) United States Patent
Perrier et al.

(10) Patent No.: US 7,419,688 B2
(45) Date of Patent: Sep. 2, 2008

(54) USE OF PLANT EXTRACTS FOR TINTING THE SKIN AS A FUNCTION OF ITS PHOTOTYPE

(75) Inventors: Eric Perrier, Les Cotes D'Arey (FR); Nabil Abdul-Malak, Caluire (FR)

(73) Assignee: Engelhard Lyon, Lyon (FR)

( * ) Notice: Subject to any disclaimer, the term of this patent is extended or adjusted under 35 U.S.C. 154(b) by 66 days.

(21) Appl. No.: 11/177,698

(22) Filed: Jul. 7, 2005

(65) Prior Publication Data

US 2006/0222619 A1 Oct. 5, 2006

(30) Foreign Application Priority Data

Mar. 31, 2005 (FR) .................... 05 03171

(51) Int. Cl.
*A01N 65/00* (2006.01)
*A61K 36/28* (2006.01)
*A61Q 1/02* (2006.01)

(52) U.S. Cl. ........................ 424/725; 424/764; 424/773; 424/59

(58) Field of Classification Search ........................ None
See application file for complete search history.

(56) References Cited

U.S. PATENT DOCUMENTS

| | | | |
|---|---|---|---|
| 6,096,316 A | 8/2000 | Vacher et al. | |
| 6,740,313 B2 * | 5/2004 | Forestier et al. | |
| 2002/0102315 A1 | 8/2002 | Leko | |
| 2002/0160065 A1 | 10/2002 | Shalaby et al. | |

FOREIGN PATENT DOCUMENTS

| | | | |
|---|---|---|---|
| ES | 2 133 244 A1 | | 9/1999 |
| FR | 2 316 885 A | | 2/1977 |
| FR | 2 595 548 A | | 9/1987 |
| FR | 2 831 438 A | | 5/2003 |
| JP | 06219958 A | * | 8/1994 |
| JP | 1007233 A | * | 3/1998 |
| JP | 2002 114700 A | | 4/2002 |
| JP | 2003055246 A | * | 2/2003 |
| JP | 2005 029536 A | | 2/2005 |
| JP | 2005 194246 A | | 7/2005 |

OTHER PUBLICATIONS

Search Report from France for Application No. FR0503171, dated Jan. 25, 2006.
Derwent Abstract No. XP-002062464 abstracting CN 930110975.

* cited by examiner

*Primary Examiner*—Michele Flood
(74) *Attorney, Agent, or Firm*—Michelle J. Burke

(57) ABSTRACT

A method for tinting, for coloring skin, or for increasing the tanned appearance of skin comprising the use of an extract of a plant from the family of Compositae or Asteraceae, preferably an extract of chicory (*Cichorium intybus* L.), and a method of screening a plant for the manufacture of a cosmetic composition for coloring, particularly for tinting, at least one part of skin.

6 Claims, No Drawings

USE OF PLANT EXTRACTS FOR TINTING THE SKIN AS A FUNCTION OF ITS PHOTOTYPE

The present invention relates to a compound for tinting the skin, which is based notably on a plant extract and/or of a mixture of plant extracts. The present invention relates in particular to the preparation of a compound which is modulated as a function of the phototype of light or mat skin to be colored.

STATE OF THE ART

DHA (dihydroxyacetone) is today one of the only molecules which is used in the fields of cosmetics for its capacity to tint the skin. The molecule does not act upon melanogenesis, but colors the skin by a reaction with the amine functions which are borne by the amino acids of the proteins and peptides of the skin. Other molecules are sometimes used in synergy with the DHA: erythrulose, which seems to increase the activity of this reaction, or AHAs (Alpha Hydroxy Acids), which seem to enable a better uniformity of the color obtained. The addition of amino acids into formulations, to enable a better control of the tint obtained on the skin, has been imagined by many formulators, without real success hitherto, since the DHA reacts with the amino acids in the formulation.

The main drawback of DHA is the appearance of color and of odor in the formulae which make use of them.

In order to avoid the drawbacks of DHA, certain tinting formulations have been imagined and proposed on the cosmetic market. These tinting solutions, which do not contain any DHA, apply to any skin without taking into consideration the various phototypes of the skin, nor taking into consideration the comparison with the natural tan of it. The consequence is that colors are obtained which are sometimes very far from a natural tan (greenish color, for example).

To this day, therefore, a cosmetic composition does not exist which is essentially without DHA, and which is adapted to the problem consisting of obtaining a modification of the color of the skin, for reproducing a natural tan, this tanning being different as a function of the phototype of the person.

AIMS OF THE INVENTION

A main aim of the invention is to solve the technical problem which consists of providing a tinting composition, particularly a coloring composition, which is based on at least one plant extract, and which enables a "healthy looking" effect to be obtained after application onto the skin surface, and particularly a skin color to be obtained which reproduces the natural color of the tan.

A particular aim of the invention is to solve the technical problem which consists of providing several tinting solutions, particularly coloring solutions, based on plant extracts, which enable, after application onto the skin surface, a skin color to be obtained which reproduces the natural color of the tan, each tinting composition being adapted to a particular phototype.

An aim of the present invention is to provide a cosmetic composition which enables a "healthy looking" effect to be obtained.

An aim of the present invention is also to provide a cosmetic composition which enables the tint of the skin to be modified, particularly in coloring the skin tissue, to obtain a coloration which is close to the natural tan.

The entirety of these technical problems is solved for the first time in a manner which is satisfactory, inexpensive, and which can be used on an industrial scale, notably in cosmetics.

DESCRIPTION OF THE INVENTION

The products originating from this invention possess a tinting effect, particularly a coloring effect, upon application onto the skin of a composition containing them.

The products of the invention adsorb onto the surface of the skin and give a color which is very close to the natural tan when they are used at an effective concentration.

When the products of the invention are used at a concentration which is less than the effective concentration, the products of the invention enable a tint to be obtained which is sufficient to have a "healthy looking" effect.

Thus, by the term "to tint", the inventors mean obtaining a change in the appearance of the skin tissue reflecting the "healthy looking" appearance, as well as obtaining a change in the appearance of the skin tissue reproducing the tanned appearance.

Advantageously, the "healthy looking" appearance is appreciated by a panel of experts.

The effective concentration can be appreciated easily by the person skilled in the art. The effective concentration enables a change to be obtained in the coloration of the skin close to that of natural tanning. In order to appreciate, with greater detail, the change in the coloration of the skin, the person skilled in the art can refer to the change in the individual typology angle, or to the change in the parameter b, as illustrated below.

The products of the present invention advantageously enable, as a function of the phototype, to reproduce a tan which is close to that obtained naturally. In particular, the products of the invention give a color which is very close to a natural tan, and can be adapted to phototypes I and II (light skins) and III and IV (mat skins).

According to a first aspect, the invention relates to a method of screening a plant extract for the manufacture of a cosmetic composition for tinting, particularly for coloring, at least one part of a skin tissue of a subject, comprising:

a) determining the change in the color intensity of a skin tissue before and after tanning;
b) applying a mixture of a plant extract or of a mixture of plant extracts onto at least one part of a skin tissue;
c) selecting the plant extract or the mixture of plant extracts which enable reproducing, in b), the change in the color intensity obtained in step a).

According to an embodiment, the invention makes use of a screening phase which is carried out on skin models which comprise at least one epidermis.

Advantageously, the skin models are biopsies or skin models which are known to the person skilled in the art.

According to another embodiment, the invention makes use of a screening phase which is carried out on human volunteers.

Preferably, the invention makes use of the two phases, preferably with a first screening phase carried out on skin models and a second phase carried out on human volunteers.

Preferably, the method of screening a plant extract for the manufacture of a cosmetic composition for tinting, particularly for coloring, at least one part of a skin tissue of a subject, comprises:

a) determining the change in the color intensity of a skin tissue before and after tanning;

b) applying a mixture of an extract of a plant from the family of Compositae or Asteraceae, preferably an extract of chicory, and of another plant extract, on at least one part of a skin tissue;

c) selecting this other plant extract when the change in the color intensity of the skin tissue before and after application in step b) reproduces the change in the color intensity obtained in step a).

Advantageously, the invention firstly consists of measuring the colors of the skin types of various phototypes, before and then after their tanning under normal conditions, and then of deducing the changes in color which are obtained according to the criteria of measurement of color which are well-known to the person skilled in the art (measurement of parameters L (brightness), a and b (decomposition of the color)).

The invention then consists in finding plants and/or extracts of plants (alone or in a mixture) which are capable of reproducing the changes in color thus observed when they are used at an effective concentration.

When the products of the invention are used at a concentration which is less than the effective concentration, the products of the invention enable a tint to be obtained which is sufficient to have a "healthy looking" effect.

Advantageously, after the selection of a plant and/or of an extract of a plant, the preparation of a composition for topical use, particularly a cosmetic composition, is carried out.

According to a second aspect, the invention also relates to a method of preparing a cosmetic composition for tinting, particularly for coloring, at least one part of a skin tissue of a subject, comprising:

a) determining the change in the color intensity of a skin tissue before and after tanning;
b) applying a mixture of a plant extract or of a mixture of plant extracts onto at least one part of a skin tissue;
c) selecting the plant extract or the mixture of plant extracts when the change in the color intensity of the skin tissue before and after application in step b) reproduces the change in the color intensity obtained in step a); and
d) formulating this plant extract or this mixture of plant extracts to obtain a cosmetic composition which enables tinting, particularly coloring, at least one part of a skin tissue of a subject.

Preferably, the method of preparing a cosmetic composition for tinting, particularly for coloring, at least one part of a skin tissue of a subject, comprises:

a) determining the change in the color intensity of a skin tissue before and after tanning;
b) applying a mixture of an extract of a plant from the family of Compositae or Asteraceae, preferably an extract of chicory, and of another plant extract on at least one part of a skin tissue;
c) selecting this other plant extract when the change in the color intensity of the skin tissue before and after application in step b) reproduces the change in the color intensity obtained in step a); and
d) formulating the mixture of the extract of this plant and of the extract of a plant from the family of Compositae or Asteraceae, preferably of the extract of chicory, to obtain a cosmetic composition for tinting, particularly for coloring, at least one part of a skin tissue of a subject.

Advantageously, the skin tissues used in step b) are as defined above.

The method cited above has enabled the recognition of compounds which are adapted to the present invention.

It has been discovered unexpectedly that an extract of a plant from the family of Compositae or Asteraceae, preferably an extract of chicory (*Cichorium intybus* L.), enables tinting, particularly coloring, a skin tissue.

Thus, according to a third aspect, the invention relates to the use of an extract of a plant from the family of Compositae or Asteraceae, preferably an extract of chicory (*Cichorium intybus* L.) (wild chicory), for tinting a skin tissue of a subject, and particularly for coloring this skin tissue, preferably for increasing its tanned or golden (yellow color) appearance.

Advantageously, the extract of a plant from the family of Compositae or Asteraceae, preferably an extract of chicory, is used in combination with another plant extract, particularly to obtain an additional tint effect, in particular an additional coloration effect, of the skin tissue. The extract of a plant from the family of Compositae enables a change to be obtained in the tint, whilst the other plant extract enables improving the change in the tint in order in particular to be adapted to the various phototypes.

According to a fourth aspect, the invention relates to the use of an extract of a plant from the family of Compositae or Asteraceae, preferably an extract of chicory, for tinting, particularly for coloring, a skin tissue of phototype I and/or II of a subject, preferably for increasing the tanned or golden (yellow color) appearance of this tissue.

Advantageously, the extract of a plant from the family of Compositae or Asteraceae, preferably an extract of chicory, is used in combination with an extract from the family of Oleaceae, such as an extract of Muirapuama or Marapuama (*Ptychoetalum olacoides*), for example.

According to a fifth aspect, the invention relates to the use of an extract of a plant from the family of Compositae or Asteraceae, preferably an extract of chicory, for tinting, particularly for coloring, a skin tissue of phototype III and/or IV of a subject, preferably for increasing the tanned appearance of this tissue.

Advantageously, the extract of a plant from the family of Compositae or Asteraceae, preferably an extract of chicory, is in combination with an extract from the family of Asclepiadaceae, such as an extract of Gymnema sylvestre, for example.

The present invention advantageously covers, according to the third, fourth or fifth aspect, the use of said extracts for reproducing the natural tan of the skin of a human being.

In particular, it is entirely advantageous to calculate the value of the individual typology angle (ITA) which is of the simplified formula:

$$ITA = \arctan[(L^* - 50)/b^*]$$

wherein $L^*$ and $b^*$ correspond to the average value of the brightness (from white +L to black −L) and of the "yellow-blue" appearance (from yellow +b to blue −b), respectively. A decrease in the ITA parameter corresponds to a darkening of the skin and to an increase in melanin pigments.

The value of the ITA parameter observed after a natural tanning is equal to about 70% of the initial ITA value. The products of the invention enable similar changes to be obtained (ITA after application for example between 50% and 90% of the initial value).

According to a sixth aspect, the invention also relates to the use of an extract of a plant from the family of Compositae or Asteraceae, preferably an extract of Chicory (*Cichorium intybus* L.), which is mixed with another plant extract to obtain a change in tint, particularly for reproducing the changes in color which are observed during natural tanning.

Advantageously, the invention relates to an extract of a plant from the family of Compositae or Asteraceae, preferably an extract of chicory, in combination with an extract of a plant selected from the group consisting of:

Menthe piperta; Malva silvestris; Cynara scolymus; Thea sinensis; juglans regia; Lawsonia inermis; Castanea vulgaris; Asarum europaeum; Leonurus cardiaca; Ballota foetida; Ocimum basilicum; Stachys officinalis; Brunella vulgaris; Calamintha officinalis; Thymus vulgaris; Rosmarinus officinalis; Humulus lupulus; Vaccinium myrtillus; Arctotaphylos uva-ursi; Calluna vulgaris; Artemisian abisinthium; Artemisia vulgaris, Artemisian abrotonum; Artemisia glacialis; Artemisia mutellina; Artemisia spicata; Chamaemelum nobile; Fraxinus excelsior; Syringa vulgaris; Jasminium grandiflorum; Lythrum salicaria; Althaea officinalis; Hysopus officinalis; Origanum majorana; Salvia officinalis; Melissa officinalis; Melittis melissophyllum; Lavandula officinalis; Quercus robur; Fagus silvatica; Nepta cataria; Origanum dictamus; Thymus serpyllum, for reproducing a natural tan on at least one part of the skin tissue of a subject.

According to a seventh aspect, the invention relates to a composition, particularly a cosmetic composition, comprising an extract of a plant from the family of Compositae or Asteraceae, preferably an extract of chicory, and an extract of a plant selected from the group defined above.

According to an eighth aspect, the invention relates to a method of preparing such a composition.

Advantageously, the method comprises preparing mixtures of plant extracts and comprises the following consecutive steps which consist in firstly manufacturing an extract of a plant from the family of Compositae or Asteraceae, preferably an extract of chicory, and an extract of another plant, particularly selected from those listed above, preferably selected from an extract of *gymnema*, an extract of *muirapuama*, and their combinations, and then in mixing them in proportions which are adapted to the phototype to be treated, such as, for example, about 65 to 85%, preferably about 75%, of extracts of plants from the family of Compositae or Asteraceae, preferably an extract of chicory, and about 15 to 35%, preferably about 25%, of other extracts of plants which are effective for modifying the coloration of the skin, notably for reproducing a natural tan.

Advantageously, the second plant extract will be selected from the group of plants consisting of:

Menthe piperta; Malva silvestris; Cynara scolymus; Thea sinensis; juglans regia; Lawsonia inermis; Castanea vulgaris; Asarum europaeum; Leonurus cardiaca; Ballota foetida; Ocimum basilicum; Stachys officinalis; Brunella vulgaris; Calamintha officinalis; Thymus vulgaris; Rosmarinus officinalis; Humulus lupulus; Vaccinium myrtillus; Arctotaphylos uva-ursi; Calluna vulgaris; Artemisian abisinthium; Artemisia vulgaris, Artemisian abrotonum; Artemisia glacialis; Artemisia mutellina; Artemisia spicata; Chamaemelum nobile; Fraxinus excelsior; Syringa vulgaris; Jasminium grandiflorum; Lythrum salicaria; Althaea officinalis; Hysopus officinalis; Origanum majorana; Salvia officinalis; Melissa officinalis; Melittis melissophyllum; Lavandula officinalis, Quercus robur; Fagus silvatica; Nepta cataria; Origanum dictamus; Thymus serpyllum.

The products according to the present invention are prepared as topical compositions, notably as cosmetic compositions or dermo-pharmaceutical compositions. From this, for these compositions, the excipient for example contains at least one compound selected from the group consisting of preservatives, emollients, emulsifiers, surfactants, moisturizers, thickeners, conditioners, matifying agents, stabilizers, antioxidants, texture agents, brightening agents, filmogenic agents, solubilizers, pigments, dyes, perfumes and solar filters. These excipients are preferably selected from the group consisting of amino acids and their derivatives, polyglycerols, esters, polymers and derivatives of cellulose, lanolin derivatives, phospholipids, lactoferrins, lactoperoxidases, sucrose-based stabilizers, E vitamins and its derivatives, natural and synthetic waxes, plant oils, triglycerides, insaponifiables, phytosterols, plant esters, silicones and its derivatives, protein hydrolyzates, jojoba oil and its derivatives, lipo/hydrosoluble esters, betaines, aminoxides, plant extracts, esters of sucrose, titanium dioxides, glycines, and parabens, and more preferably from the group consisting of butylene glycol, steareth-2, steareth-21, glycol-15 stearyl ether, cetearyl alcohol, phenoxyethanol, methylparaben, ethylparaben, propylparaben, butylparaben, butylene glycol, natural tocopherols, glycerol, sodium dihydroxycetyl, isopropyl hydroxycetyl ether, glycol stearate, triisononaoine, octyl cocoate, polyacrylamide, isoparaffin, laureth-7, a carbomer, propylene glycol, glycerol, bisabolol, dimethicone, sodium hydroxide, PEG 30-dipolyhydroxysterate, capric/caprylic triglycerides, cetearyl octanoate, dibutyl adipate, grape seed oil, jojoba oil, magnesium sulphate, EDTA, cyclomethicone, xanthan gum, citric acid, sodium lauryl sulphate, mineral waxes and oils, isostearyl isostearate, propylene glycol dipelargonate, propylene glycol isostearate, PEG 8 Beeswax, hydrogenated palm tree heart oil glycerides, hydrogenated palm oil glycerides, lanolin oil, sesame oil, cetyl lactate, lanolin alcohol, castor oil, titanium dioxide, lactose, sucrose, low density polyethylene, and an isotonic saline solution.

Advantageously, the compositions mentioned above are formulated in a form selected from the group consisting of a solution, which is aqueous or oily, a cream or an aqueous gel or an oily gel, notably in a pot or in a tube, notably a shower gel, a shampoo; a milk; an emulsion, a microemulsion or a nanoemulsion, which is notably oil-in-water or water-in-oil or multiple or silicone-containing; a lotion, notably in a glass bottle, a plastic bottle, a measure bottle, an aerosol; an ampoule; a liquid soap; a dermatological bar; an ointment; a foam; and an anhydrous product, preferably which is liquid, pasty or solid, e.g. in a form of a stick, notably in a form of lipstick.

Other aims, features and advantages of the invention will appear clearly to the person skilled in the art upon reading the explanatory description which makes reference to the Examples which are given simply as an illustration and which in no way limit the scope of the invention.

The Examples make up an integral part of the present invention, and any feature which appears novel with respect to any prior state of the art from the description taken in its entirety, including the Examples, makes up an integral part of the invention in its function and in its generality.

Thus, every example has a general scope.

Furthermore, in the Examples, all percentages are given by weight, unless indicated otherwise, temperature is expressed in degrees Celsius unless indicated otherwise, and the pressure is atmospheric pressure, unless indicated otherwise.

EXAMPLES

Example 1

Skin Colors Obtained Before and After Natural Tanning, by Phototype

The color of the skin of volunteers was measured (in triplicate), before and after natural tanning, by a colorimetric technique with the aid of a Chromameter CR300 (Minolta, Japan). The chromametry enables the objective quantification of changes in colors. The measurements are given as three parameters: L, a and b, wherein L measures the brightness (from white +L to black −L), a measures the <<red green>> appearance (from red +a to green −a), and b measures the <<yellow blue>> appearance (from yellow +b to blue −b)

From these parameters, it was possible to calculate the Individual Typology Angle or ITA, defined by the following simplified formula:

$$I.T.A.=\arc\tang[(L^*-50)/b^*]$$

L*, a*, and b* meaning the average of the value of L, a, and of b, respectively.

Phototypes I and II

Before natural tanning (before summer holidays)

|                    | L     | a    | b     | ITA  |
|--------------------|-------|------|-------|------|
| Average n = 10     | 62.72 | 9.95 | 18.45 | 0.71 |
| Standard deviation | 2.67  | 1.03 | 2.26  | 0.22 |

After natural tanning (after summer holidays)

|                    | L     | a    | b     | ITA  |
|--------------------|-------|------|-------|------|
| Average n = 10     | 61.07 | 9.57 | 20.08 | 0.57 |
| Standard deviation | 3.15  | 2.34 | 2.05  | 0.20 |

Phototypes III and IV

Before natural tanning (before summer holidays)

|                    | L     | a     | b     | ITA  |
|--------------------|-------|-------|-------|------|
| Average n = 10     | 56.21 | 11.39 | 20.77 | 0.30 |
| Standard deviation | 3.07  | 0.96  | 1.37  | 0.16 |

After natural tanning (after summer holidays)

|                    | L     | a     | b     | ITA  |
|--------------------|-------|-------|-------|------|
| Average n = 10     | 54.54 | 10.90 | 22.25 | 0.22 |
| Standard deviation | 4.49  | 1.46  | 1.49  | 0.22 |

It is observed that that the parameter a varies little, whereas L decreases (the skin darkens) and that b increases (the skin passes from blue to yellow). Consequently, the ITA index decreases after exposure to the sun, i.e. after a natural tan is obtained.

The natural tanning thus induces a decrease in the ITA parameter; the ITA value after tanning is on average between 70 and 80% of the initial value.

Example 2 a) Preparation of Extracts

A—Preparation of an Extract of a Plant from the Family of Compositae or Asteraceae, (Extract of Chicory)

1) Introduce, into aqueous phase, the chicory plant, preferably the root of chicory, after grinding (e.g. introduce, into 95 g of water, 5 g of root at ambient temperature for 48 hours);
2) The extract is then filtered;
3) The filtrate obtained is concentrated by vaporization.
4) A chicory paste is obtained.

B—Preparation of an Extract from the Family of Asclepiadaceae (Gymnema)

1) Introduce, into aqueous phase, the Gymnema plant, preferably the leaves of Gymnema, after grinding (e.g. introduce, into 95 g of water, g of leaves at ambient temperature for 48 hours);
2) The extract is then filtered;
3) An extract of Gymnema is obtained.

C—Preparation of an Extract from the Family of Oleaceae (Muirapuama)

1) Introduce, into aqueous phase, the Muirapuama plant, preferably the stem and/or the root of Muirapuama, after grinding (e.g. introduce, into 95 g of water, 5 g of stem and/or of root at ambient temperature for 48 hours);
2) The extract is then filtered;
3) An extract of Muirapuama is obtained.

The extracts of the other plants can be obtained in a similar manner.

Starting from a mixture of the 2 extracts, the chicory and Muirapuama, a tan is in particular obtained which is very close to the natural tan for phototypes I and II, called phototypes for light skins.

Starting from a mixture of the 2 extracts, the chicory and Gymnema, a tan is obtained in particular which is very close to the natural tan for phototypes III and IV, called phototypes for mat skins.

b) Preparation of a Mixture of an Extract of Chicory and of an Extract from the Family of Oleaceae (Muirapuama), Demonstration of the tinting effect on light skins 1—A preparation of a mixture of an extract of Chicory and of extract of Muirapuama was carried out at the rate of 75% of extract of Chicory for 25% of extract of Muirapuama.
2—Said preparation was used at 5% in a hydro-alcohol solution (such as, for example, a water-ethanol mixture).
3—Principle of measurement of tinting effect by a calorimetric technique.

The products tested were applied at the rate of 5 µl/cm$^2$ and the color of the skin of the volunteers was measured in triplicate by a colorimetric technique with the aid of a Chromameter CR300 (Minolta, Japan). The chromametry enables the objective quantification of changes in colors. The measurements are given as three parameters L, a and b as indicated above.

A coloring effect could be justified if the color of the skin was modified after the application of the product tested, manifesting itself by an increase in the parameter b and a decrease in the parameter L.

The Individual Typology Angle or ITA was calculated:

A decrease in this ITA parameter corresponds to a darkening of the skin and to an increase in the melanin pigments.

Phototypes I and II
Before application of the mixture

|  | L | a | b | ITA |
|---|---|---|---|---|
| Average n = 10 | 68.03 | 7.40 | 13.64 | 1.38 |
| Standard deviation | 2.14 | 1.29 | 2.28 | 0.39 |

After application of the mixture

|  | L | a | b | ITA |
|---|---|---|---|---|
| Average n = 10 | 64.80 | 8.63 | 17.70 | 0.86 |
| Standard deviation | 2.39 | 1.13 | 1.96 | 0.22 |

As in the case of a natural tan, it is observed that the parameter a varies little, that the parameter b increases (a more yellow skin), and that the parameter L decreases (a darker skin).

It is thus noted that the ITA value obtained after application of the mixture onto light skins of phototypes I and II is equal to about 62% of the initial value. This corresponds to a change in the color of the skin which is comparable to the change in the color of the skin during a natural tanning.

c) Preparation of a Mixture of an Extract of Chicory and of an Extract from the Family of Asclepiadaceae (Gymnema). Demonstrating the Tinting Effect on Mat Skins 1—A preparation of a mixture of an extract of Chicory and of extract of Gymnema was carried out at the rate of 75% of extract of Chicory for 25% of extract of Gymnema.
2—Said preparation was used at 5% in a hydro-alcohol solution (such as, for example, a water-ethanol mixture).
3—Principle of measurement of tinting effect by a calorimetric technique.

Phototypes III and IV:
Before application of the mixture

|  | L | a | b | ITA |
|---|---|---|---|---|
| Average n = 10 | 63.33 | 9.07 | 16.02 | 0.84 |
| Standard deviation | 2.86 | 1.38 | 1.67 | 0.23 |

After application of the mixture

|  | L | a | b | ITA |
|---|---|---|---|---|
| Average n = 10 | 61.18 | 9.53 | 18.68 | 0.60 |
| Standard deviation | 2.41 | 0.84 | 1.25 | 0.15 |

As in the case of a natural tan, it is observed that the parameter a varies little, that the parameter b increases (a more yellow skin), and that the parameter L decreases (a darker skin).

It is thus noted that the ITA value obtained after application of the mixture onto mat skins of phototypes III and IV is equal to about 71% of the initial value. This corresponds to a change in the color of the skin which is comparable to the change in the color of the skin during a natural tanning.

Example 3

Preparation of a Mixture of an Extract of *Cichorium intybus* L. and of *Ptychopetalum Olacoides*

A preparation of a mixture of an extract of Chicory and of extract of *Ptychopetalum Olacoides* was carried out at the rate of 75% of extract of Chicory (see Example 2 for the method of preparation of the extract) per 25% of extract of *Ptychopetalum Olacoides* (e.g. aqueous extract made with 5 g of plant, preferably the stems and/or roots, and 95 g of water, at ambient temperature for 48 hours).

Said preparation was used at 5% in a hydro-alcohol solution.

The results obtained are similar to those obtained in Example 2b.

Example 4

Preparation of a Mixture of an Extract of *Cichorium intybus* L. and of Gymnema Sylvestre A preparation of a mixture of an extract of Chicory and of extract of Gymnema Sylvestre was carried out at the rate of 75% of extract of Chicory (see Example 1 for the method of preparation of the extract) per 25% of extract of Gymnema Sylvestre (e.g. aqueous extract made with 5 g of plant, preferably the leaves, and 95 g of water, at ambient temperature for 48 hours).

Said preparation was used at 5% in a hydro-alcohol solution.

The results obtained are similar to those obtained in Example 2c.

Example 5

Preparation of a Mixture of an Extract of *Cichorium intybus* L. and of an Extract from the Family of Comoositae (or Asteraceae) and Particularly of *Cynara Scolymus*

During step 1 of Example 3 and or 4, an extract of *Cynara Scolymus* is prepared (e.g. aqueous extract made with 5 g of plant, preferably the leaves, and 95 g of water, at ambient temperature for 48 hours).

All the other steps are identical.

The results obtained are similar to those obtained in Example 2c.

Example 6

Preparation of a Mixture of an Extract of *Cichorium intybus* L. and of an Extract from the Family of Labiaceae and Particularly of *Mentha Piperta*

During step 1 of Example 3 and or 4, an extract of *Mentha Piperta* is prepared (e.g. aqueous extract made with 5 g of plant, preferably the leaves, and 95 g of water, at ambient temperature for 48 hours).

All the other steps are identical.

The results obtained are similar to those obtained in Example 2b.

Example 7

Preparation of a Mixture of an Extract of *Cichorium intybus* L. and of an Extract from the Family of Malvaceae and Particularly of *Malva Silvestris*

During step 1 of Example 3 and or 4, an extract of *Malva Silvestris* is prepared (e.g. aqueous extract made with 5 g of plant, preferably the leaves, and 95 g of water, at ambient temperature for 48 hours).

All the other steps are identical.

The results obtained are similar to those obtained in Example 2c.

Example 8

Preparation of a Mixture of an Extract of *Cichorium intybus* L. and of an Extract from the family of Ternstroemiaceae and Particularly of *Thea Sinensis*

During step 1 of Example 3 and or 4, an extract of *Thea Sinensis* is prepared (e.g. aqueous extract made with 5 g of plant, preferably the leaves, and 95 g of water, at ambient temperature for 48 hours).

All the other steps are identical.

The results obtained are similar to those obtained in Example 2c.

Example 9

Preparation of a Mixture of an Extract of *Cichorium intybus* L. and of an Extract from the Family of Juglandaceae and Particularly of *Juglans Regia*

During step 1 of Example 3 and or 4, an extract of *Juglans Regia* is prepared (e.g. aqueous extract made with 5 g of plant, preferably the leaves, and 95 g of water, at ambient temperature for 48 hours).

All the other steps are identical.

The results obtained are similar to those obtained in Example 2b.

Example 10

Preparation of a Mixture of an Extract of *Cichorium intybus* L. and of an Extract from the Family of Lythraceae and particularly of *Lawsonia Inermis*

During step 1 of Example 3 and or 4, an extract of *Lawsonia Inermis* is prepared (e.g. aqueous extract made with 5 g of plant, preferably the leaves, and 95 g of water, at ambient temperature for 48 hours).

All the other steps are identical.

The results obtained are similar to those obtained in Example 2b.

Example 11

Preparation of a Mixture of an Extract of *Cichorium intybus* L. and of an Extract from the Family of Fagaceae and Particularly of *Castanea Vulgaris*

During step 1 of Example 3 and or 4, an extract of Castanea Vulgaris is prepared (e.g. aqueous extract made with 5 g of plant, preferably the leaves, and 95 g of water, at ambient temperature for 48 hours).

All the other steps are identical.

The results obtained are similar to those obtained in Example 2c.

Example 12

Other Plants Selected for Their Capacities to Color the Skin

The whole of the following plants was selected on the basis of the criteria of the present invention, and particularly on the technical effect that these plants bring about in reproducing the natural tan of the skin. In each case, the corresponding aqueous extracts were made according to the method described above (e.g. 5 g of plant, 95 g of water, extraction at ambient temperature for 48 hours, filtration and use of the extract).

*Menthe piperta* (preferably leaves),
*Malva silvestris* (preferably leaves),
*Cynara scolymus* (preferably leaves),
*Thea sinensis* (preferably leaves),
*Juglans regia* (preferably leaves),
*Lawsonia inermis* (preferably leaves),
*Castanea vulgaris* (preferably leaves),
*Asarum europaeum* (preferably leaves),
*Leonurus cardiaca* (preferably flowers),
*Ballota foetida* (preferably flowers),
*Ocimum basilicum* (preferably flowers and/or leaves),
*Stachys officinalis* (preferably roots and/or leaves),
*Brunella vulgaris* (preferably flowers and/or leaves and/or stems),
*Calamintha officinalis* (preferably leaves and/or stems),
*Thymus vulgaris* (preferably leaves),
*Rosmarinus officinalis* (preferably leaves),
*Humulus lupulus* (preferably cones),
*Vaccinium myrtillus* (preferably berries),
*Arctotaphylos uva-ursi* (preferably leaves),
*Calluna vulgaris* (preferably flowers),
*Artemisian abisinthium* (preferably flowers),
*Artemisia vulgaris* (preferably roots and/or leaves),
*Artemisian abrotonum* (preferably leaves and/or stems),
*Artemisia glacialis* (preferably roots and/or flowers),
*Artemisia mutellina* (preferably roots and/or flowers),
*Artemisia spicata* (preferably roots and/or flowers),
*Chamaemelum nobile* (preferably stems and/or flowers),
*Fraxinus excelsior* (preferably bark),
*Syringa vulgaris* (preferably leaf),
*Jasminium grandiflorum* (preferably flower),
*Lythrum salicaria* (preferably stems and/or flowers and/or leaf),
*Althaea officinalis* (preferably roots and/or leaves),
*Hysopus officinalis* (preferably flowers),
*Origanum majorana* (preferably leaf),

*Salvia officinalis* (preferably leaf),
*Melissa officinalis* (preferably leaf),
*Melittis melissophyllum* (preferably stems and/or flowers and/or leaf),
*Lavandula officinalis* (preferably flowers),
*Quercus robur* (preferably bark),
*Fagus silvatica* (preferably bark),
*Nepta cataria* (preferably stems and/or flowers and/or leaf),
*Origanum dictamus* (preferably stems and/or flowers and/or leaf),
*Thymus serpyllum* (preferably flowers), Example 13

Use of a Mixture of an Extract of Chicory (*Cichorium Intybus*) or of a Plant from the Family of Compositae, Combined Either with an extract of Gymnema(Gymnema Sylvestre) or an extract from the family of Asclepiadaceae,
Or with an extract of Muirapuama (*Ptychopetalum Olacoides*) or an extract from the family of Oleaceae.

In this way, it is possible to prepare compositions which comprise 75% of an extract of chicory (*Cichorium Intybus*) or of a plant from the family of Compositae, and 25% of an extract from the family of Asclepiadaceae such as, for example, Gymnema(*Gymnema Sylvestre*), or from the family of Oleaceae such as, for example, *Muirapuama (Ptychopetalum Olacoides*).

The composition obtained is entirely effective to obtain modifications of the color of the skin which are similar to those obtained during a natural tanning.

Example 14

Example of a Formulation Containing the Products of the Invention

Use of the products of the invention in cosmetic or pharmaceutical formulations of oil-in-water emulsion type Formulation 14a:

| water | qsp 100 |
|---|---|
| Butylene Glycol | 2 |
| Glycerine | 3 |
| Sodium Dihydroxycetyl Phosphate, Isopropyl Hydroxycetyl Ether | 2 |
| Glycol Stearate SE | 14 |
| Triisononaoin | 5 |
| Octyl Cocoate | 6 |
| Butylene Glycol, Methylparaben, Ethylparaben, Propylparaben, pH adjusted to 5.5 | 2 |
| Products of the invention | 0.01-20% |

Formulation 14b:

| Water | qsp 100 |
|---|---|
| Butylene Glycol | 2 |
| Glycerine | 3 |
| Polyacrylamide, Isoparaffin, Laureth-7 | 2.8 |
| Butylene Glycol, Methylparaben, Ethylparaben, Propylparaben; | 2 |
| Phenoxyethanol, Methylparaben, Propylparaben, Butylparaben, Ethylparaben | 2 |
| Butylene Glycol | 0.5 |
| Products of the invention | 0.01-20% |

Formulation 14c:

| Carbomer | 0.50 |
|---|---|
| Propylene Glycol | 3 |
| Glycerol | 5 |
| Water | qsp 100 |
| Octyl Cocoate | 5 |
| Bisabolol | 0.30 |
| Dimethicone | 0.30 |
| Sodium Hydroxide | 1.60 |
| Phenoxyethanol, Methylparaben, Propylparaben, Butylparaben, Ethylparaben | 0.50 |
| Perfume | 0.30 |
| Products of the invention | 0.01-20% |

Example 15

Use of the Products of the Invention in a Water-in-Oil Type Formulation

| PEG30-dipolyhydroxystearate | 3 |
|---|---|
| Capric Triglycerides | 3 |
| Cetearyl Octanoate | 4 |
| Dibutyl Adipate | 3 |
| Grape Seed Oil | 1.5 |
| Jojoba Oil | 1.5 |
| Phenoxyethanol, Methylparaben, Propylparaben, Butylparaben, Ethylparaben | 0.5 |
| Glycerine | 3 |
| Butylene Glycol | 3 |
| Magnesium Sulfate | 0.5 |
| EDTA | 0.05 |
| Water | qsp 100 |
| Cyclomethicone | 1 |
| Dimethicone | 1 |
| Perfume | 0.3 |
| Products of the invention | 0.01-20% |

Example 16

Use of the Products of the Invention in a Formulation of Shampoo or Shower Gel Type

| Xanthan Gum | 0.8 |
|---|---|
| Water | qsp 100 |
| Butylene Glycol, Methylparaben, Ethylparaben, Propylparaben | 0.5 |

-continued

| | |
|---|---|
| Phenoxyethanol, Methylparaben, Propylparaben, Butylparaben, Ethylparaben | 0.5 |
| Citric acid | 0.8 |
| Sodium Laureth Sulfate | 40.0 |
| Product of the invention | 0.01-20% |

Example 17

Use of the Products of the Invention in a Formulation of Aqueous Gels (Eve Surrounds, Slimmers, etc . . . )

| | |
|---|---|
| Water | qsp 100 |
| Carbomer | 0.5 |
| Butylene Glycol | 15 |
| Phenoxyethanol, Methylparaben, Propylparaben, Butylparaben, Ethylparaben | 0.5 |
| Products of the invention | 0.01-20% |

Example 18

Toxicological Studies of the Products of the Invention

Evaluation of the Cosmetic Acceptance of a Preparation Containing the Subject of the Invention Toxicology tests were carried out on the compound obtained according to Example 2 or 3 incorporated at 10% in a 0.5% xanthan gel, by an ocular evaluation in the rabbit, by the study of the absence of abnormal toxicity by single oral administration in the rat and by the study of the sensitizing power in the guinea pig.

Evaluation of the Primary Irritation of the Skin in the Rabbit

The preparations described above are applied without dilution at the dose of 0.5 ml on the skin of 3 rabbits according to the method recommended by the OECD Directive in relation to the study of <<the acute irritant/corrosive effect on the skin >>.

The products are classed according to the criteria defined in the Decision of Jan. 2, 1982 published in the Official Journal of the French Republic (the "JORF") of Feb. 21, 1982.

Evaluation of the Ocular Irritation in the Rabbit

The preparations described above were instilled pure and in one batch at the rate of 0.1 ml in the eye of three rabbits according to the method recommended by the directive of the OECD No. 405 of 24 Feb. 1987 relating to the study of the "acute irritant/corrosive effect on the eyes".

The results of this test enable concluding that the preparations can be considered as non-irritant for the eyes, in the sense of Directive 91/326 EEC, used pure or without dilution.

Test on the Absence of Abnormal Toxicity by Single Oral Administration in the Rat The preparations described were administered in one batch orally at the dose of 5 g/Kg of body weight, to 5 male rats and 5 female rats of a protocol inspired from the directive of the OECD No. 401 of $24^{th}$ Feb. 1987 and adapted to cosmetic products.

The LD0 and LD50 are found to be greater than 5,000 mg/Kg. The preparations tested are therefore not classed amongst the preparations which are dangerous by ingestion.

Evaluation of the Skin Sensitization Potential in the Guinea Pig

The preparations described are subjected to the maximization test described by Magnusson and Kligmann, a protocol which is in agreement with the directive line No. 406 of the OECD.

The preparations described in the preceding Examples are classed as non-sensitizing by contact with the skin.

What is claimed is:

1. A method of producing an appearance of a natural tan on at least one part of skin comprising applying onto said skin an effective amount of a topical composition, wherein said topical composition comprises an aqueous root extract of *Cichorium intybus*, a second plant extract selected from the group consisting of:
an aqueous leaf extract of *Gymnema sytvestre*, and an aqueous stem or root extract of *Ptychopetalum olacoides*, and a topically acceptable excipient.

2. The method of claim 1 wherein said second plant extract is an aqueous stem or root extract of *Ptychopetalum olacoides*.

3. The method of claim 1 wherein said second plant extract is an aqueous leaf extract of extract of *Gymnema sylvestre*.

4. The method of claim 1 wherein said composition comprises about 65% to about 85%, by weight of chicory extract and about 15% to about 35%, by weight of said second plant extract.

5. The method of claim 1 wherein an individual typology angle of said skin after application of said topical composition is between 50% and 90% of the individual typology angle of said skin before application of said topical composition.

6. The method of claim 1 wherein the skin is either phototype I or phototype II and the second plant extract is an aqueous stem or root extract of *Ptychopetalum olacoides*.

* * * * *